United States Patent [19]

Gerhaeuser et al.

[11] Patent Number: 4,763,287

[45] Date of Patent: Aug. 9, 1988

[54] MEASURING PERFORMANCE INFORMATION IN RUNNING DISCIPLINES AND SHOE SYSTEMS

[75] Inventors: Heinz Gerhaeuser, Waischenfeld; Gerhard Pirner, Etzelwang; Thomas Rueckert, Hausen, all of Fed. Rep. of Germany

[73] Assignee: PUMA AG Rudolf Dassler Sport, Herzogenaurach, Fed. Rep. of Germany

[21] Appl. No.: 52,061

[22] Filed: May 21, 1987

[30] Foreign Application Priority Data

May 24, 1986 [DE] Fed. Rep. of Germany ....... 3617591

[51] Int. Cl.$^4$ .................. G01C 22/00; G08B 23/00
[52] U.S. Cl. .................. 364/561; 235/105; 272/100; 340/323 R; 364/413
[58] Field of Search .......... 36/132, 136; 73/489, 73/490, 491; 235/105; 272/70, 100; 364/413, 415, 561, 562, 565, 705, 709; 340/323 R

[56] References Cited

U.S. PATENT DOCUMENTS

| | | | |
|---|---|---|---|
| 4,053,755 | 10/1977 | Sherrill | 235/105 |
| 4,144,568 | 3/1979 | Hiller et al. | 364/413 |
| 4,367,473 | 1/1983 | Marin et al. | 364/561 |
| 4,371,945 | 2/1983 | Karr et al. | 340/323 R |
| 4,387,437 | 6/1983 | Lowrey et al. | 364/565 |
| 4,571,680 | 2/1986 | Wu | 235/105 |
| 4,579,769 | 3/1986 | Frederick | 364/565 |
| 4,651,446 | 3/1987 | Yukawa et al. | 36/132 |
| 4,703,445 | 10/1987 | Dassler | 364/561 |

*Primary Examiner*—Patrick R. Salce
*Assistant Examiner*—Jeffrey Sterrett
*Attorney, Agent, or Firm*—Sixbey, Friedman, Leedom & Ferguson

[57] ABSTRACT

A process and system for measuring information concerning movement factors, and to values, which can be calculated therefrom, particularly stride length, stride number, stride time and running time, via a pair of shoes (1, 2), each of which is provided with a transmitter (S1 or S2), a receiver (E1 or E2), and a signal time measuring device (counter Z1 or Z2). A direct signal ($t_{dir.}$) emitted by the front shoe (1) in response to ground contact is received by the rearward shoe (2), is transferred in conformance to time parameters to the first shoe 1 as a reflected signal (refl.). The direct and reflected signals as well as the readouts of both counters (Z1 and Z2) are transmitted to a computer unit, particularly, a high-frequency computer unit for use in determination of the movement information.

20 Claims, 3 Drawing Sheets

MEASURING PERFORMANCE INFORMATION IN RUNNING DISCIPLINES AND SHOE SYSTEMS

BACKGROUND OF THE INVENTION

The present invention relates to a process and shoe system for measuring information concerning moving sequences in running disciplines, and to value which can be calculated based thereon, particularly information concerning stride length, stride rate, stride time, and running time determined with the aid of a pair of running shoes having a transmitter and receiver in each shoe as well as a sensor which triggers emission of a signal when one of the shoes makes contact with the ground.

A process and system of this kind is disclosed in German Offenlegungsschrift No. 34 05 081 (which corresponds to the present assignee's allowed U.S. Pat. No. 4,703,445), wherein the forward shoe emits a first signal to the rearward shoe, each time there is ground impact with the shoe, while simultaneously transmitting an activation signal to a remote computer unit. The rearward shoe subsequently sends a second signal to the forward shoe, and from there, to the computer unit. Based on the time delay between receipt of these two signals, information concerning the leg or running speed, and/or stride length of the runner can be detected and emitted. In commonly assigned U.S. Pat. No. 4,736,312, a further development of this system is disclosed wherein the jump or flight time of the wearer's stride (occurring during a leap phase wherein both feet are off the ground) can be considered as well. To this end, a second sensor is provided in the other shoe to detect when the trailing foot is lifted off from the ground and, based upon the time and origin of signals from both shoes, movement characteristics of the user are determined.

SUMMARY OF THE INVENTION

It is the primary objective of the present invention to improve the accuracy of such a measuring process and system, and further, to provide that the process and system simultaneously provide information concerning leap time and concerning values which can be derived therefrom in a simple and accurate manner.

This objective is achieved in accordance with the features of the preferred embodiments described herein. In accordance with particular features, a first counter is provided in a first shoe that is activated upon ground impact of the first shoe and deactivated upon receipt of a reflected signal from the second shoe, while a second counter is provided in the second shoe which is activated during lift-off of the second shoe and deactivated based upon receipt of the ground contact signal of the first shoe.

The use of two counters in combination with the transmitting-receiving devices permits measurement of the leap time and the signal travel time easily and accurately, and with a minimum of components.

Another means for simplifying the process and system is the use of a basic transmitter-receiver converter, which can be effectively switched from the transmitting to the receiving mode.

These and further objects, features and advantages of the present invention will become more obvious from the following description when taken in connection with the accompanying drawings which show, for purposes of illustration only, several embodiments in accordance with the present invention.

DETAILED DESCRIPTION OF THE PREFERRED EMBODIMENT

Figure 1:
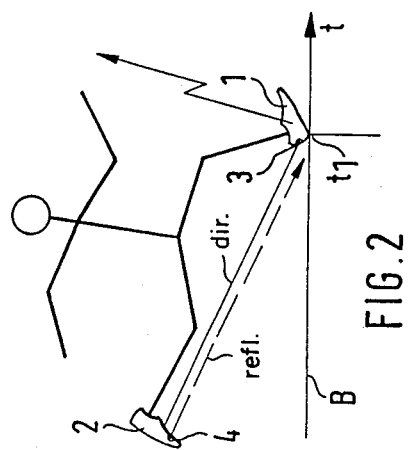
FIG. 1 schematically depicts the start of the runner's leap phase at the time of rearward foot lift-off and initiation of the process of the invention.

FIG. 1 shows the position of a first shoe 1 (which happens to be forwardly directed) relative to a second shoe 2 (which happens to be rearwardly directed) at a point in time to which, for describing the invention, will be considered the commencement of the process and is occurring at initiation of the leap phase.

Figure 2:
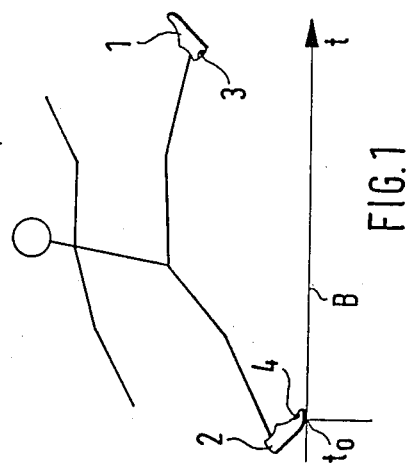
FIG. 2 schematically depicts the end of the leap phase when the forward foot is put down on the ground.

FIG. 2 shows the relative positions assumed by shoes 1, 2 at a subsequent time $t_1$, at which the jump phase initiated in FIG. 1 is completed.

Figure 4:
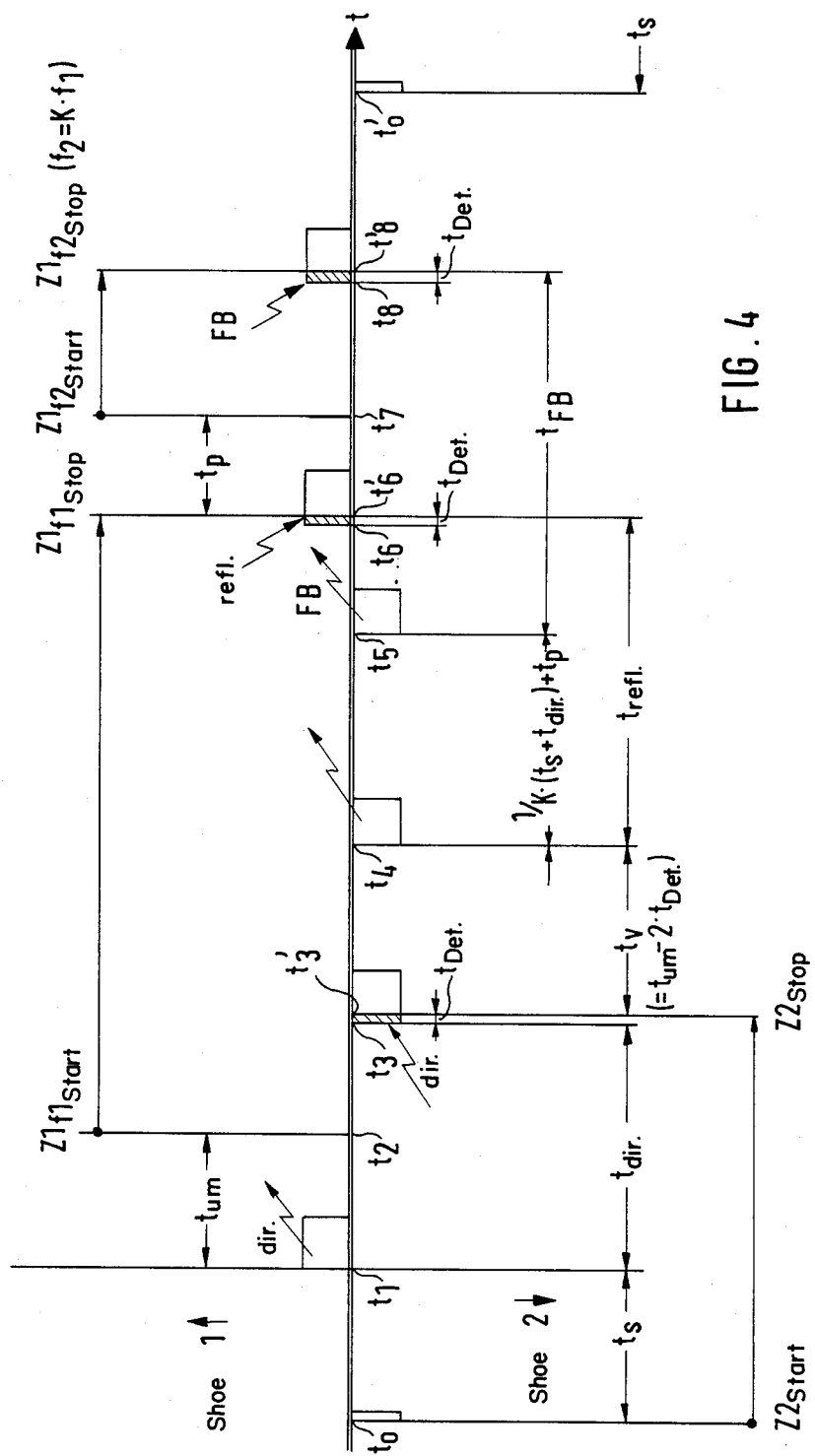
FIG. 4 is a flow chart depicting performance of the inventive process with the system of the preferred embodiment.

In FIG. 4 the signals transmitted and received at the first shoe 1 are depicted above time axis t, and those emitted by the second shoe 2 are shown below axis t, during various time segments.

Figure 3:
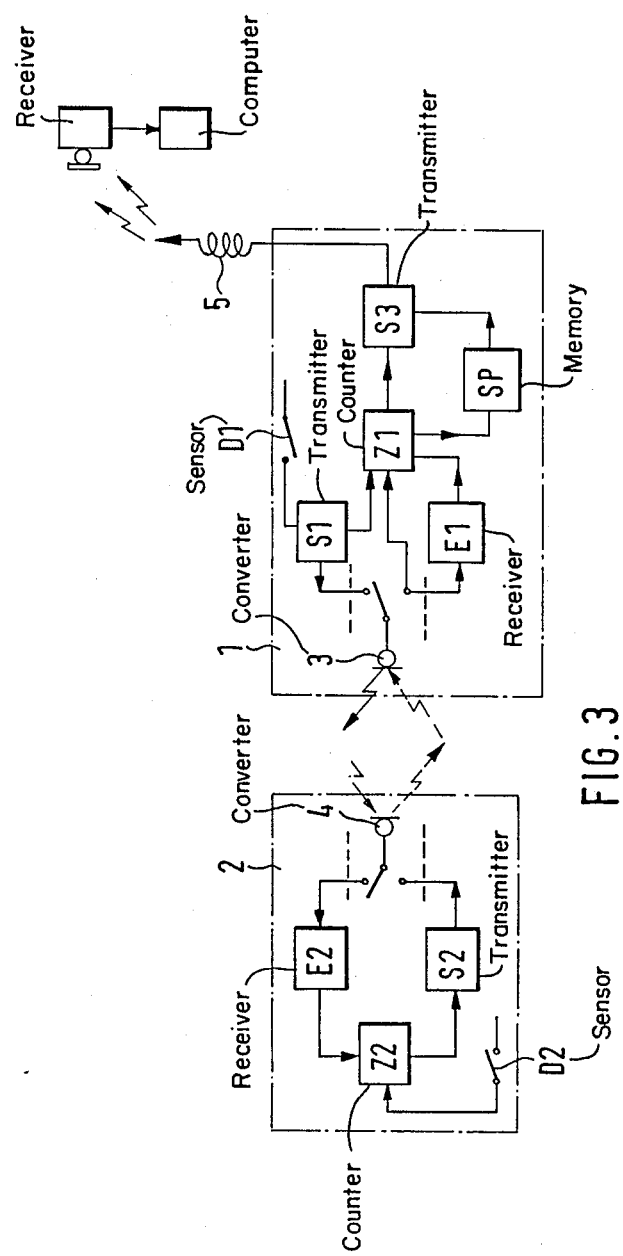
FIG. 3 illustrates a basic switch diagram of the transmitter and receiver devices of the shoe system of the invention.

Each shoe 1 and 2, respectively, is provided with a transmitter unit and a receiver unit S1, E1, S2, E2 (FIG. 3), particularly units which function on an ultrasonic basis. Advantageously, only one converter 3 or 4, respectively, is provided in this case, the converter being capable of operating in both transmitting and receiving modes. The changeover from one mode to the other occurs in the respective transmitter-receiver units S1, E1 or S2, E2. It is also preferable if both transmitter-receiver units S1, E1 or S2, E2 are constructed in the same manner.

A pressure sensor D1, D2 is provided in each shoe. Upon ground impact of first shoe 1, pressure sensor D1 of the first shoe 1 causes emission of an output signal dir. (direct ray) from transmitter S1 and which is delivered to receiver E2 from converter 4. After emission of the output signal dir., the receiver E1 is coupled to converter 3 and upon receipt of the output signal dir., in shoe 2, converter 4 is switched from its receiving to its transmitting mode, whereafter a reflected output signal refl. is emitted from shoe 2 to first shoe 1, where it is subsequently received by converter 3 and receiver E1.

Moreover, each shoe 1, 2 contains a time-measuring device (counter Z1, Z2 and first shoe 1, additionally, is provided with storage means SP for storing at least one value transferred from the counter. Additionally, another transmitter S3 is provided in first shoe 1, which is capable of transmitting data obtained from the counters Z1, Z2 of the first shoe 1 and the second shoe 2, which may have been stored temporarily in storage means SP, to a remote computer.

The operating mode of such arrangement is described by way of the flow sheet, depicted in FIG. 4 as follows:

Second counter Z2 is activated via pressure sensor D2 at time point $t_o$ of the running period (FIG. 1) at which a leap phase, when neither shoe 1, 2 touches ground B, commences by second shoe 2 lifting off ground B.

After leap time $t_s$, shoe 1 hits ground B at time point $t_1$ (FIG. 2), which causes pressure sensor D1 to address transmitter S1 and to emit direct ray dir. as an output signal to rearward shoe 2 via converter 3. After transmittal of output signal dir., converter 3 is connected to receiver E1 during switch-over period $t_{um}$, effecting a change to the receiving mode, with first counter Z1 being started at time point $t_2$.

After time $t_{dir.}$ of output signal dir. has elapsed, this signal is received by converter 4 at time point $t_3$ and is processed in receiver E2, whereby the signal to be processed is available after a detection period, for example, after the transient process of the receiving circuit, at time point $t'_3$. This signal is utilized for stopping the second counter Z2. Accordingly, the value at counter Z2 represents leap time $t_s$ plus travel time of direct ray $t_{dir.}$ from first shoe 1 to second shoe 2, plus detection time $t_{det.}$ (between points $t_3$, $t'_3$).

After a delay time $t_v$ in second transmitter-receiver S2, E2, a reflected output signal refl. is emitted from shoe 2 to shoe 1 at time point $t_4$ by transmitter S2 via converter 4. Signal refl. is received at shoe 1 after a travel time $t_{refl.}$ at time point $t_6$. The corresponding signal is available at time point $t'_6$, again, only after a detection time $t_{det.}$ has elapsed. This signal is utilized to stop first counter Z1.

By selecting the delay time $t_v$ to equal the switch-over time $t_{um}$, the value at counter Z1 corresponds exactly to the sum comprised of the travel time of output signals dir. and refl., i.e., $t_{dir.} + t_{refl.}$.

In accordance with the features of the invention, the value at second counter Z2 is emitted to shoe 1 after release of the reflected output signal refl., after time point $t_4$. This occurs here by the emission of a sequential burst FB (or time multiplex signal) at time point $t_5$, subsequent to a corresponding time lag from $t_4$ to $t_5$, representing leap time $t_s$ plus the travel time of direct output signal $t_{dir.}$ plus, if appropriate, an interval time $t_p$.

In this case, interval time $t_p$ is equal to the time interval from time point $t'_6$ at which the first counter Z1 was stopped to time point $t_7$, at which time first counter Z1 is restarted.

After travel time $t_{FB}$ has elapsed, sequential burst FB is received by receiver E1 at time point $t_8$, whereby the processing signal is available at time point $t'_8$ after detection time $t_{det.}$. At this point, the first counter Z1 is stopped by sequential burst FB.

During time interval $t_p$, the first value determined by counter Z1 is stored in a storage unit of storage means SP.

Starting with time point $t'_6$, additional transmitter S3 of shoe 1 is activated and the value which is stored in storage SP, and, subsequently, also the second computed value corresponding to time $t_{FB}$, are emitted to a remote receiver R, from which they are fed to a remote computer unit C. Advantageously, the transmitter S3 is a transmitter of high-frequency electromagnetic wavelength, while the radiating means 5 consists of an appropriate antenna.

Accordingly, information concerning the double travel time of direct output signal dir. and the leap time $t_s$, which is increased by the amount of the single travel time $t_{dir.}$, are already available in the computer, and prior to that time, are available in first shoe 1. Information as to the actual leap time $t_s$ can be obtained from this data, whereby it is advantageous if such information is obtained in the microprocessor of the remote computer unit after the emission of the values to the remote computer unit since the arithmetic necessary therefor can be carried out by it without any difficulty.

In order to ensure transmittal of the values recorded at the second counter Z2 in the short time available, such transmittal occurs during a time frame which is reduced by a factor K. At the same time, first counter Z1 is addressed at a frequency $f_2$ during its second counting period which is increased by factor K relative to the frequency $f_1$ utilized in its first counting period. Accordingly, the transmittal time between time points $t_4$ and $t_5$ is: $1/K \cdot (t_s + t_{dir.}) + t_p$.

If the user of the inventive process and system changes his motion from running to walking, the leap phase, and inherently, the leap time $t_s$, are eliminated. Time point $t_o$ in every case then is after time point $t_1$. Second counter Z2 having been started is not stopped by direct output signal dir. in this instance and, accordingly, is permitted to run down (assuming use of a countdown type timer). In correspondence therewith, there is no recording of leap time, no transmittal of sequential burst FB, and, thus, no signal to stop counter Z1 which has been activated a second time. This causes counter Z1 also to run down, and the only value transmitted to the computer unit is the value $t_{dir.} + t_{refl.}$, which was obtained during the first activation of counter Z1. Unless both shoes are provided with lift-off and contact detecting and signaling arrangements (which is not the case in the illustrated system), the above processing will occur only every other stride, i.e., will not occur in the stride from when shoes 1 and 2 are reversed relative to their positions shown in FIGS. 1, 2. However, by computation, with the frequency rate as a given factor, the sum of travel times $t_{dir.} + t_{refl.}$ provides information concerning the double distance of shoes 1 and 2, and, consequently, the double stride length.

In order to increase the transmittal accuracy, it is advantageous to transmit the signals emitted from the first shoe 1 to the remote computer unit in a suitable code, permitting recognition and correction of transmittal errors. In similar manner, the leap time $t_s$ recorded at shoe 2 can be transmitted to shoe 1 in encoded form.

It is noted that, with respect to aspects of this invention that are in common with corresponding aspects of the initially mentioned commonly assigned U.S. patent applications, reference may be made thereto for further details. For example, Ser. No. 701,194 shows manners for mounting sensors, transmitters, etc. in a shoe sole.

While we have shown and described various embodiments in accordance with the present invention, it is understood that the same is not limited thereto, but is susceptible of numerous changes and modifications as known to those skilled in the art, and we, therefore, do not wish to be limited to the details shown and described therein, but intend to cover all such changes and modifications as are encompassed by the scope of the appended claims.

What is claimed is:

1. In a process, for determining information pertaining to movement factors in running disciplines and values derived therefrom, particularly information concerning stride length, stride rate, stride time and running time, with a pair of running shoes, each shoe of which contains a transmitter and a receiver, of the type wherein a first one of said shoes, upon contacting the ground, emits a first output signal to a second one of said shoes, said first signal being triggered by a ground contact sensor, and wherein the receiver contained in said second shoe receives said first signal and emits a reflected output signal via the transmitter of the second shoe to the receiver of the first shoe, whereafter the first shoe emits a second output signal to a remote receiver that is linked with a computer unit, and wherein a determination of desired information is computed and displayed by the computer unit data based on the relative timing of the first and second signals, the improvement comprising the additional steps of activating a first counter when said first shoe contacts the ground and deactivating said first counter in response to receipt of the reflected output signal by the receiver of the first shoe; activating a second counter when said second shoe lifts off at the ground by a sensor built into said second shoe and deactivating said second counter in response to receipt of the first output signal from the first shoe by the receiver of the second shoe; emitting a value determined by the second counter to the receiver of the first shoe; and utilizing readouts from said counters in said determination.

2. Process according to claim 1, wherein at least a portion of said signals is encoded.

3. Process according to claim 1, wherein said transmitting and receiving of said signals by the shoes are performed by a transmitter-receiver unit of each shoe which has a single transmitter-receiver-converter which is operable in both transmitting and receiving operating modes.

4. Process according to claim 3, wherein the first counter is activated after a delay time which corresponds to a switch time for switching the transmitter-receiver unit from the transmitting mode to the receiving mode, and wherein the reflected output signal is emitted after a delay time which approximates said switch time.

5. Process according to claim 4, wherein said delay time for emission of the reflected output signal equals the switch time minus the transient time of the receivers of the first and second shoe.

6. Process according to claim 5, wherein at least a portion of said signals is encoded.

7. Process according to claim 6, wherein the signals are transmitted between the first and second shoes in the form of ultrasonic impulses and wherein ultrasonic converters are used as converters.

8. Process according to claim 7, wherein the signals emitted to the remote computer unit by the first shoe are transmitted as high-frequency electromagnetic waves.

9. Process according to claim 6, wherein the time during which both shoes are out of contact with the ground is computed and displayed by the computer unit based upon the relative travel times of the signals, counter actuation delay times, and said interval.

10. Process according to claim 6, wherein the signals emitted to the remote computer unit by the first shoe are transmitted as high-frequency electromagnetic waves.

11. Process according to claim 3, wherein the signals are transmitted between the first and second shoes in the form of ultrasonic impulses and wherein ultrasonic converters are used as converters for the transmitter-receiver units.

12. Process according to claim 11, wherein the signals emitted to the remote computer unit by the first shoe are transmitted as high-frequency electromagnetic waves.

13. Process according to claim 1, wherein, after an interval subsequent to deactivation of a first counting period of the first counter, the value determined by the first counter is stored and, then, the first counter is reactivated for a second counting period; and wherein the transmitter of the second shoe emits a deactivation signal to the first shoe, after a time corresponding to the value determined by the second counter plus said interval, for deactivating the first counter.

14. Process according to claim 13, wherein the time which corresponds to the value determined by the second counter is lower than said value by a factor K, and a counter frequency rate of the first counter is increased for said second counter period, relative to the counting frequency of the first counter during the first counting period, by this factor K.

15. System for the determination of movement characteristics in running disciplines, such as stride length, running speed or the like with shoes, especially athletic shoes, comprising:
(a) first and second shoes;
(b) first sensor means, in said first shoe, for responding to contacting of the first shoe with the ground;
(c) second sensor means, in said second shoe, for responding to lifting-off of the second shoe with the ground;
(d) first transmitter means, in said first shoe, linked to said first sensor means and being activatable for radiating a first signal by a response from the first sensor means;
(e) second transmitter means, in said second shoe, for radiating second and third signals;
(f) receiver means in said second shoe for receiving the first signal, said receiver means in said second shoe processing said first signal and triggering issuance of said second signal;
(g) receiver means in said first shoe for receiving the second and third signals;
(h) first counter means in said first shoe, said first counter being linked to said first sensor means for being activatable by a response from said first sensor means and being linked to the receiver means of the first shoe for being deactivatable by receipt of said second signal by said receiver means of the first shoe;
(i) second counter means, in said second shoe, said second counter being linked to the second sensor means for being activatable by a response from said second sensor means, being linked to said receiver means of the second shoe for being deactivatable by receipt of said first signal by the receiver means of the second shoe means, and being linked to said second transmitter means for emitting a value determined by said second counter as said third signal; and
(j) means for performing said determination of movement characteristics utilizing value determined by said counters.

16. System according to claim 15, wherein the transmitting means and receiving means of each shoe are comprised of a single transmitter-receiver-converter unit that is operable in both transmitting and receiving operating modes.

17. System according to claim 16, wherein the transmitter-receiver-converter units transmit, receive, and convert ultrasonic pulses serving as said first, second and third signals.

18. System according to claim 17, further comprising a high frequency electromagnetic wave transmitter in said first shoe and linked to said first counter for transmitting values determined by said counter to said means for performing, said means for performing comprising a remote receiver and computer means linked thereto.

19. System according to claim 18, further comprising storage means linked to said first counter means and said electromagnetic wave transmitter for storing a first value determined by said first counter means and for releasing it to said electromagnetic wave transmitter.

20. System according to claim 15, comprising an additional transmitter and a storage means in said first shoe, said additional transmitter and said storage means being linked with each other and the first counter means for transmitting signals corresponding to values determined by the counters to said means for performing and wherein said means for performing comprises a remote receiver and computer means linked thereto.

* * * * *